(12) United States Patent
Akagane

(10) Patent No.: US 12,186,006 B2
(45) Date of Patent: Jan. 7, 2025

(54) ENERGY TREATMENT DEVICE AND METHOD FOR MANUFACTURING ENERGY TREATMENT DEVICE

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 1167 days.

(21) Appl. No.: 16/906,049

(22) Filed: Jun. 19, 2020

(65) Prior Publication Data
US 2020/0315696 A1    Oct. 8, 2020

Related U.S. Application Data

(63) Continuation of application No. PCT/JP2017/045936, filed on Dec. 21, 2017.

(51) Int. Cl.
*A61B 18/14* (2006.01)
*A61B 18/00* (2006.01)

(52) U.S. Cl.
CPC ............ *A61B 18/1445* (2013.01); *A61B 2018/00077* (2013.01); *A61B 2018/0013* (2013.01); *A61B 2018/00136* (2013.01); *A61B 2018/0072* (2013.01); *A61B 2018/00732* (2013.01)

(58) Field of Classification Search
CPC .......... A61B 2018/00136; A61B 2018/00107; A61B 2018/0013
See application file for complete search history.

(56) References Cited

U.S. PATENT DOCUMENTS

| | | | |
|---|---|---|---|
| 5,380,320 A | 1/1995 | Morris | |
| 6,056,735 A * | 5/2000 | Okada | A61B 17/320092 606/1 |
| 7,896,875 B2 * | 3/2011 | Heim | A61B 18/1402 606/45 |
| 2001/0012936 A1 | 8/2001 | Heim et al. | |

(Continued)

FOREIGN PATENT DOCUMENTS

| | | |
|---|---|---|
| JP | 2004-520906 A | 7/2004 |
| JP | 2007-070682 A | 3/2007 |

(Continued)

OTHER PUBLICATIONS

Nov. 14, 2022 Office Action issued in Chinese Application No. 201780097881.5.

(Continued)

*Primary Examiner* — Linda C Dvorak
*Assistant Examiner* — Ryan T Clark
(74) *Attorney, Agent, or Firm* — Oliff PLC

(57) ABSTRACT

An energy treatment device includes: a base having electrical conductivity and including a treatment surface for applying a high-frequency current to a treatment target when being supplied with electrical energy. A coating, including a silane coupling agent having a coupling structure, is formed over at least the treatment surface of the base by a bond due to the coupling structure; and an organic layer is disposed between the treatment surface of the base and the coating, and is bonded to the surface of the base. The coupling structure of the coupling agent of the coating is bonded to the organic layer.

15 Claims, 5 Drawing Sheets

(56) References Cited

U.S. PATENT DOCUMENTS

| | | |
|---|---|---|
| 2006/0259032 A1 | 11/2006 | Nesbitt |
| 2009/0030438 A1 | 1/2009 | Stulen |
| 2009/0143806 A1* | 6/2009 | Witt .................. A61L 31/14 |
| | | 427/2.28 |
| 2011/0206321 A1* | 8/2011 | Reever ................ G02B 6/3624 |
| | | 385/38 |
| 2012/0029514 A1 | 2/2012 | Fairbourn et al. |
| 2015/0265305 A1* | 9/2015 | Stulen .................. A61B 17/285 |
| | | 606/169 |

FOREIGN PATENT DOCUMENTS

| | | |
|---|---|---|
| JP | 2010-82144 A | 4/2010 |
| WO | 2014/068688 A1 | 5/2014 |
| WO | 2017/126051 A1 | 7/2017 |

OTHER PUBLICATIONS

Jun. 23, 2020 International Preliminary Report on Patentability issued in International Application No. PCT/JP2017/045936.

Mar. 13, 2018 International Search Report issued in International Patent Application No. PCT/JP2017/045936.

* cited by examiner

ENERGY TREATMENT DEVICE AND METHOD FOR MANUFACTURING ENERGY TREATMENT DEVICE

CROSS-REFERENCE TO RELATED APPLICATIONS

This is a Continuation Application of PCT Application No. PCT/JP2017/045936, filed Dec. 21, 2017, the entire contents of which are incorporated herein by reference.

BACKGROUND

An energy treatment device for treating a treatment target, such as living tissue, by applying a high-frequency current to the treatment target from the treatment surface is known. In such energy treatment devices, at least a part of the treatment surface is formed of an electro-conductive material. Electrical energy, upon being supplied to the electro-conductive material with the treatment surface in contact with the treatment target, allows a high-frequency current to pass through the treatment surface to the treatment target.

A coating for preventing sticking can be applied to the treatment surface. However, depending on the thickness of the coating, the impedance of the applied coating may affect the application of a high-frequency current to the treatment target.

SUMMARY

The present disclosure relates generally to an energy treatment device for treating a treatment target using treatment energy, and a method for manufacturing the energy treatment device.

According to an exemplary embodiment, an energy treatment device includes: a base having electrical conductivity and including a treatment surface for applying a high-frequency current to a treatment target when supplied with electrical energy. A coating including a silane coupling agent having a coupling structure, is formed over at least the treatment surface of the base by a bond due to the coupling structure. An organic layer is disposed between the surface of the base and the coating, and is bonded to the surface of the base. The coupling structure of the coupling agent of the coating is bonded to the organic layer.

According to another exemplary embodiment, a method of manufacturing an energy treatment device includes: forming a base which has electrical conductivity and which includes a treatment surface for applying a high-frequency current to a treatment target when supplied with electrical energy; forming an organic layer on at least the treatment surface of the base by bonding a coupling structure of a titanate coupling agent to at least the treatment surface of the base; and forming a coating over at least the treatment surface of the surface of the base by bonding a coupling structure of a silane coupling agent to the organic layer.

DETAILED DESCRIPTION

An exemplary embodiment of the present disclosure will be described with reference to FIGS. 1 to 5.

Figure 1:
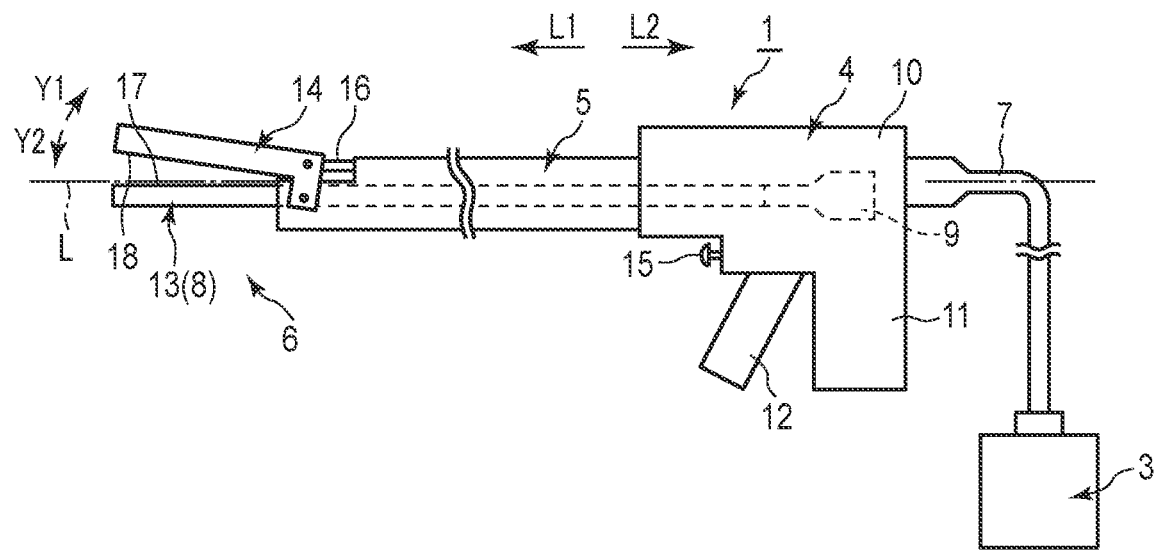
FIG. 1 is a schematic view of an energy treatment device according to an exemplary embodiment.

FIG. 1 is a diagram showing a treatment device 1 that is an energy treatment device of this embodiment. As shown in FIG. 1, the treatment device 1 includes a housing 4 and a cylindrical shaft 5 connected to the housing 4. The housing 4 can be held. The housing 4 is connected to one end of a cable 7. The other end of the cable 7 is detachably connected to a power supply device 3.

The shaft 5 defines longitudinal axis L. Here, the direction along longitudinal axis L is defined as the longitudinal direction. One side in the longitudinal direction is referred to as a distal side (arrow L1 side in FIG. 1), and the opposite side to the distal side is referred to as a proximal side (arrow L2 side in FIG. 1). The shaft 5 extends from the proximal side to the distal side along longitudinal axis L and is connected to the distal side of the housing 4.

The shaft 5 has a distal section provided with an end effector 6. The end effector 6 includes a first gripping piece 13 and a second gripping piece 14. The first gripping piece 13 and the second gripping piece 14 are configured to open and close with respect to each other. In this embodiment, the first gripping piece 13 is supported by the shaft 5, and the second gripping piece 14 is attached to the shaft 5 rotatably with respect to the first gripping piece 13.

The first gripping piece 13 includes a treatment surface (facing surface) 17 that faces the second gripping piece 14 and applies treatment energy to a treatment target. The second gripping piece 14 includes a treatment surface (facing surface) 18 that faces the treatment surface 17 of the first gripping piece 13 and applies treatment energy to a treatment target.

The directions in which the end effector 6 opens and closes intersect (are perpendicular to or substantially perpendicular to) longitudinal axis L. Of the opening and closing directions of the end effector 6, the direction in which the second gripping piece 14 opens with respect to the first gripping piece 13 is defined as an opening direction (arrow Y1) of the second gripping piece 14, and the direction in which the second gripping piece 14 closes with respect to the first gripping piece 13 is defined as a closing direction (arrow Y2) of the second gripping piece 14. Here, the direction that intersects (are perpendicular to or substantially perpendicular to) longitudinal axis L and intersects (are perpendicular to or substantially perpendicular to) the opening and closing directions of the end effector 6 is defined as a width direction of the end effector 6.

The housing 4 includes a housing main body 10 and a grip (fixed handle) 11. The housing main body 10 extends along longitudinal axis L. The grip 11 extends from the housing main body 10 toward the side away from longitudinal axis L. The shaft 5 is connected to the housing main body 10 from the distal side.

A movable handle 12 is rotatably attached to the housing main body 10. The movable handle 12 is located on the grip 11 side with respect to longitudinal axis L, and is located on the distal side with respect to the grip 11 in this embodiment. When the movable handle 12 pivots with respect to the housing main body 10, the movable handle 12 opens or closes with respect to the grip 11. When the movable handle 12 opens or closes with respect to the grip 11, an operation of opening or closing the end effector 6 as described above is input through the movable handle 12. That is, the movable handle 12 is an open/close operation input unit.

The movable handle 12 and the second gripping piece 14 are connected through a movable member 16. The movable member 16 extends within the shaft 5 along longitudinal axis L. Opening or closing the movable handle 12 with respect to the grip 11 causes the movable member 16 to move along longitudinal axis L with respect to the shaft 5 and the housing 4, and the second gripping piece 14 to pivot with respect to the shaft 5. In this manner, the gripping pieces 13 and 14 open or close with respect to each other. The treatment target is gripped between the gripping pieces 13 and 14 by closing the gripping pieces 13 and 14 with the treatment target disposed between the gripping pieces 13 and 14.

In one embodiment, the movable handle 12 is on the proximal side with respect to the grip 11. In another embodiment, the movable handle 12 is located on the side opposite to the grip 11 with respect to longitudinal axis L, and moves in a direction intersecting (perpendicular to or substantially perpendicular to) longitudinal axis L in the open and close operations.

In yet another embodiment, an operating member, such as a rotary knob, is attached to the housing main body 10. In this case, pivoting the operating member on longitudinal axis L with respect to the housing 4 allows the shaft 5 and the end effector 6 together with the operating member to rotate about longitudinal axis L with respect to the housing 4.

The power supply device 3 includes a high-frequency power supply and an ultrasonic power supply. The high-frequency power supply includes a waveform generator, conversion circuitry, and a transformer, etc. and converts power from a battery power source, an outlet power source, or the like into high-frequency power. As will be described later, at least a part of each of the first gripping piece 13 and the second gripping piece 14 is formed of an electro-conductive material. The high-frequency power supply is electrically connected to the electro-conductive material of each of the first and second gripping pieces 13 and 14 via an electrical path provided through the inside of the cable 7, the inside of the housing 4, and the inside of the shaft 5. The high-frequency power supply outputs the high-frequency power obtained from the power conversion through the aforementioned electrical path, and supplies the high-frequency power as electrical energy to the first gripping piece 13 and the second gripping piece 14.

The ultrasonic power supply includes a waveform generator, a conversion circuit, and a transformer, etc. and converts power from a battery power source, an outlet power source, or the like into alternating current power. An ultrasonic transducer 9 and a vibration transmitting member (probe) 8 connected to the ultrasonic transducer 9 from the distal side are provided inside the housing main body 10. The ultrasonic power supply is electrically connected to the ultrasonic transducer 9 via an electrical path provided through the inside of the cable 7 and the inside of the housing 4. The ultrasonic transducer 9, upon being supplied with electric energy (AC power) from the ultrasonic power supply, generates ultrasonic vibration. The ultrasonic vibration generated with the ultrasonic transducer 9 is transmitted to the vibration transmitting member 8.

The vibration transmitting member 8 extends from the inside of the housing main body 10 to the distal side, passes through the inside of the shaft 5, and protrudes from the distal end of the shaft 5 toward the distal side. The first gripping piece 13 is formed by the protrusion of the vibration transmitting member 8 from the shaft 5 toward the distal side. The ultrasonic vibration generated by the ultrasonic transducer 9 is transmitted to the distal end of the vibration transmitting member 8, forming the first gripping piece 13. As a result, the ultrasonic vibration is transmitted to the first gripping piece 13 as treatment energy. The vibration transmitting member 8 is preferably formed of a material having electrical conductivity and high vibration-transmitting properties. In this embodiment, the vibration transmitting member 8 is formed of a titanium alloy, which is compatible with living tissue. The vibration transmitting member 8 may be formed of a metal material other than a titanium alloy, such as duralumin or stainless steel.

The housing main body 10 is provided with an operation button 15. The operation button 15 is an energy operation input unit. When an operation is input through the operation button 15 with a treatment target being gripped between the gripping pieces 13 and 14, the treatment device 1 is supplied with electric energy from, for example, each of the high-frequency power supply and the ultrasonic power supply. Then, high-frequency current and ultrasonic vibration are applied as treatment energy to the gripped treatment target. In one example, instead of or in addition to the operation button 15, a foot switch electrically connected to the power supply device 3 is provided separately from the treatment device 1.

In another example, the housing main body 10 is provided with a plurality of operation buttons 15. When an operation is input through one of the plurality of operation buttons 15 with a treatment target being gripped, only high-frequency current is applied to the treatment target as treatment energy, for example. Further, when an operation is input through another one of the plurality of operation buttons 15 with a treatment target being gripped, high-frequency current and ultrasonic vibration are applied to the treatment target as treatment energy, for example.

Figure 2:
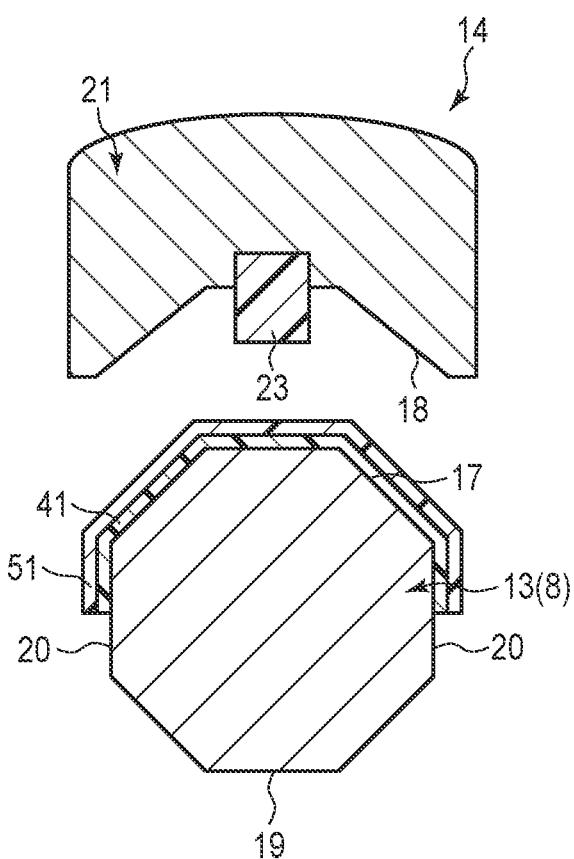
FIG. 2 is a schematic view of a cross section intersecting the longitudinal axis of an end effector according to an exemplary embodiment.

FIG. 2 is a view of a cross section intersecting (are perpendicular to or substantially perpendicular to) longitudinal axis L of the end effector 6. The first gripping piece 13 is electrically conductive. The first gripping piece 13 is formed of metal, for example. In this embodiment, the first gripping piece 13 is formed by the protrusion of the vibration transmitting member 8 from the shaft 5 toward the distal side, and is formed of a titanium alloy. The first gripping piece 13 includes a treatment surface 17, a back surface 19 facing the opposite side to the treatment surface 17, and a pair of side surfaces 20 facing outward in the width direction of the end effector 6.

In this embodiment, the vibration transmitting member 8 is a base material having electrical conductivity and forming the treatment surface 17. Further, in this embodiment, the first gripping piece 13 is formed of the base.

The vibration transmitting member 8 is connected to one end of an electrical path formed of an electrical line etc. inside the housing main body 10. This electrical path extends through the inside of the housing 4 and the inside of the cable 7, and is connected to the high-frequency power supply of the power supply device 3 at the other end. The vibration transmitting member 8 is electrically connected to the high-frequency power supply via this electrical path. This makes it possible to supply high-frequency power from the high-frequency power supply to the first gripping piece 13. The first gripping piece 13, upon being supplied with the high-frequency power, serves as a first electrode.

The second gripping piece (gripping member) 14 includes a support (jaw) 21. The support 21 is connected to the shaft 5 so as to be pivotal on the shaft 5. The support 21 has electrical conductivity. The support (electro-conductive member) 21 is formed of, for example metal. The support 21 forms part of the treatment surface 18.

The support 21 is connected to one end of an electrical path formed of, for example, an electrical line. This electrical path extends through the inside of the shaft 5, the inside of the housing 4, and the inside of the cable 7, and is connected to the high-frequency power supply of the power supply device 3 at the other end. The support 21 and the high-frequency power supply are electrically connected via this electrical path. This makes it possible to supply high-frequency power from the high-frequency power supply to the support 21. The support 21, upon being supplied with the high frequency power, serves as a second electrode different from the first electrode.

The second gripping piece 14 includes a short-circuit preventing member (pad member) 23. The short-circuit preventing member 23 is attached to the support 21 from the gripping piece 13 side. The short-circuit preventing member 23 is disposed at the center of the gripping piece 14 in the width direction and forms a center portion of the treatment surface 18. The short-circuit preventing member 23 has electrical insulation properties. The short-circuit preventing member 23 is formed of, for example, a resin material.

When the gripping pieces 13 and 14 are closed with respect to each other, the short-circuit preventing member 23 of the gripping piece 14 is in contact with the treatment surface 17 of the gripping piece 13. In this state, a gap is formed between the support 21 and the treatment surface 17 of the gripping piece 13, and the treatment surface 17 of the gripping piece 13 is not in contact with the support 21. Therefore, in a state where the support 21 and the gripping piece 13 serve as electrodes, a short circuit is effectively prevented from occurring in electric circuitry in which high-frequency power is outputted from the power supply device 3 to the support 21 and the gripping piece 13.

An organic layer 41 and an anti-sticking coating (coating) 51 are formed on the surface of the first gripping piece 13. The organic layer 41 is provided between the anti-sticking coating 51 and the surface of the first gripping piece 13. The organic layer 41 is a monomolecular film formed with a surface modifier on the surface of the first gripping piece 13. The organic layer 41 is bonded to each of the surfaces of the first gripping piece 13 and the anti-sticking coating 51, thereby bringing the first gripping piece 13 and the anti-sticking coating 51 into adhesion. The anti-sticking coating 51 is a monomolecular film formed on the surface of the organic layer 41.

In this embodiment, the organic layer 41 and the anti-sticking coating 51 are provided in the region where the treatment surface 17 is provided in the longitudinal direction. Further, the organic layer 41 and anti-sticking coating 51 are formed in a region including the treatment surface 17 in the surface (outer peripheral surface) about longitudinal axis L of the first gripping piece 13. The organic layer 41 and anti-sticking coating 51 are provided on the treatment surface 17 and part of the side surfaces 20 in the outer peripheral surface of the first gripping piece 13.

Figure 3:
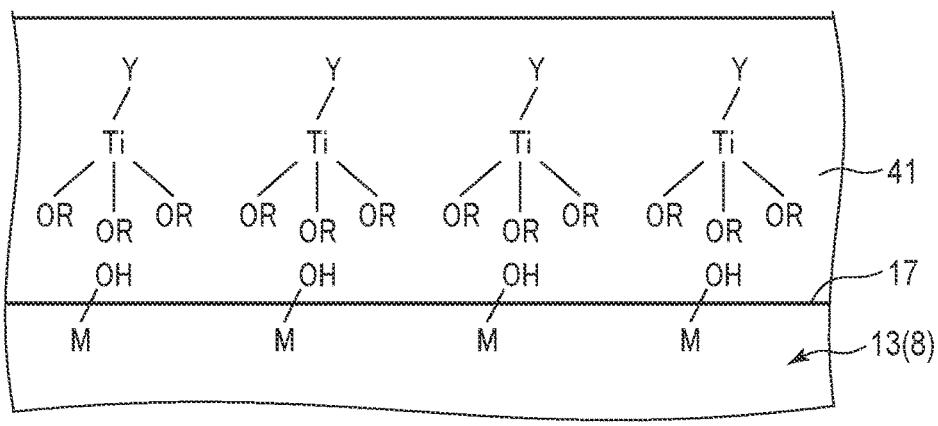
FIG. 3 schematically illustrates the process of forming an organic layer on a treatment surface according to an exemplary embodiment.

The organic layer 41 and the anti-sticking coating 51 will be described with reference to FIGS. 3 to 5. As shown in FIG. 3, the surface of the first gripping piece 13 is covered with hydroxyl groups OH due to the reaction of metal matrix M with oxygen and moisture in the atmosphere. In this embodiment, metal matrix M is titanium.

The organic layer 41 is formed of a material containing a titanate coupling agent. The titanate coupling agent of this embodiment includes a titanium atom Ti, one or more hydrolyzable groups OR, and an organic functional group Y. The titanium atom Ti and three hydrolyzable groups OR form a coupling structure of the titanate coupling agent.

Each of the hydrolyzable groups OR is chemically bonded to the titanium atom Ti. The hydrolyzable group OR is a reactive group which is to be chemically bonded to an inorganic material by hydrolysis etc., and is, for example, an alkoxy group, such as a methoxy group, an ethoxy group, etc. The organic functional group Y is chemically bonded to the titanium atom Ti. The organic functional group Y is a functional group that is to be bonded to an organic material, and is, for example, a vinyl group, an epoxy group, an amino group, a methacrylic group, or a mercapto group. In one embodiment, an amino group (an amine reactive group), for example, is used as the organic functional group Y. In this case, $OC_2H_4NHC_2H_4NH_2$, for example, is used as the organic functional group Y.

Figure 4:
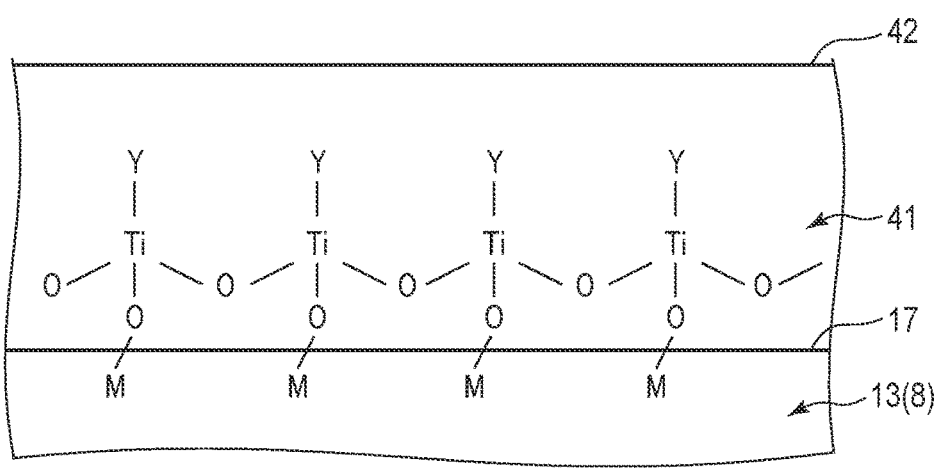
FIG. 4 schematically illustrates a state where the organic layer is formed on the treatment surface according to an exemplary embodiment.

As shown in FIG. 4, in the surface of the first gripping piece 13, the coupling structure of the titanate coupling agent is bonded to the surface of the first gripping piece 13. The coupling structure of the titanate coupling agent being bonded to the surface of the first gripping piece 13 forms the organic layer 41 on the surface of the first gripping piece 13.

Here, the bond between the coupling structure of the titanate coupling agent and the surface of the first gripping piece 13 may be a chemical bond (by hydrolysis) between a hydrolyzable group OR of the titanate coupling agent and a hydroxyl group OH on the surface of the first gripping piece 13, a bond by chemisorption, a bond by intermolecular force, or a bond by other interactions.

The organic functional groups Y of the titanate coupling agent form a modified surface 42 over the surface of the first gripping piece 13. In this embodiment, the modified surface 42 is formed of organic functional groups Y such as amine groups.

Figure 5:
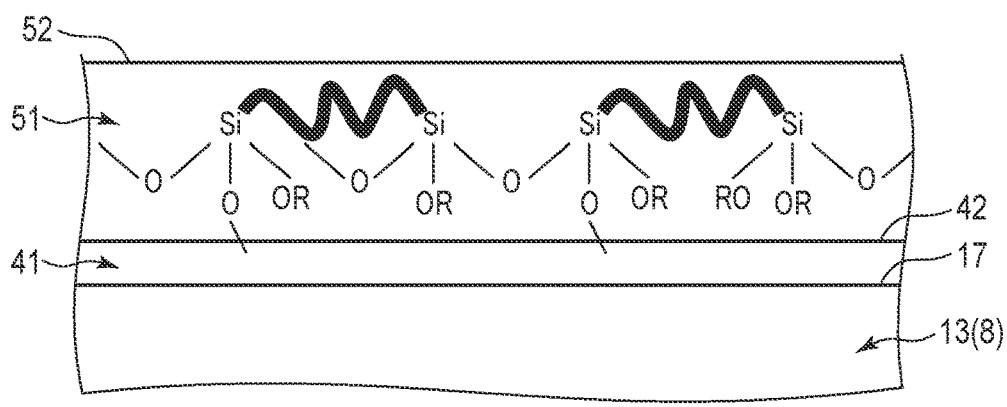
FIG. 5 schematically illustrates a state where an anti-sticking coating is formed over the treatment surface according to an exemplary embodiment.

As shown in FIG. 5, the anti-sticking coating 51 is formed of a material containing a silane coupling agent. The silane coupling agent includes a silicon atom Si, a molecular chain containing a carbon atom C and a fluorine atom F, and a hydrolyzable group OR.

In the silane coupling agent, three hydrolyzable groups OR are each chemically bonded to the silicon atom Si. In the silane coupling agent, the three hydrolyzable groups OR being chemically bonded to the silicon atom Si forms a coupling structure. The coupling structure is provided at each end of the molecular chain.

In the molecular chain, a fluorine atom F etc. is bonded to carbon atoms C bonded in a chain form. The hydrolyzable group OR is a reactive group which is to be chemically bonded to an inorganic material by hydrolysis etc., and is, for example, an alkoxy group, such as a methoxy group, an ethoxy group, etc.

Over the surface of the first gripping piece 13, the coupling structure of the silane coupling agent is bonded to the organic functional group Y (e.g., amine group) forming the modified surface 42 of the organic layer 41. The silane coupling agent being bonded to the organic layer 41 forms the anti-sticking coating 51 over the surface of the first gripping piece 13 through the organic layer 41.

Here, the bond between the silane coupling agent and the modified surface 42 of the organic layer 41 includes a chemical bond between a hydrolyzable group OR of the silane coupling agent and the organic functional group Y (an amine group) of the titanate coupling agent, and a chemical bond (by hydrolysis) between the hydrolyzable group OR of the silane coupling agent and the hydroxyl group OH of the modified surface 42, a bond by chemisorption, a bond by intermolecular force, and a bond by other interaction.

Next, a step of forming the organic layer 41 and anti-sticking coating 51 on the surface of the first gripping piece 13 including the treatment surface 17 in manufacturing of the treatment device 1 will be described. When forming the organic layer 41 and anti-sticking coating 51 on the treatment surface 17, an operator first applies the titanate coupling agent to the surface of the first gripping piece 13 (see FIG. 3). The titanate coupling agent is accordingly bonded to the surface of the first gripping piece 13 as described above, which forms the organic layer 41 of the monomolecular film (see FIG. 4). The modified surface 42 is formed over the surface of the first gripping piece 13 through the organic layer 41.

Next, the operator applies the silane coupling agent onto the modified surface 42 formed over the surface of the first gripping piece 13. The coupling structure of the silane coupling agent is accordingly bonded to the modified surface 42 of the organic layer 41 as described above, which forms the anti-sticking coating 51 (see FIG. 5).

As described above, the organic layer 41 and the anti-sticking coating 51 are formed in a region including part of the side surfaces 20 and the treatment surface 17 in the outer peripheral surface of the first gripping piece 13 around the extended axis of the first gripping piece 13 (see FIG. 2). In the step of forming the organic layer 41 and the anti-sticking coating 51, the organic layer 41 and the anti-sticking coating 51 are formed in a desired region of the surface of the first gripping piece 13, for example by masking the portions other than the portion where the organic layer 41 and the anti-sticking coating 51 are intended to be formed.

Next, the operation and effect of the treatment device 1 of this embodiment will be described. When performing treatment using the treatment device 1, first, the end effector 6 is inserted into a body cavity such as an abdominal cavity. Then, a treatment target, such as a blood vessel, is disposed between the paired gripping pieces 13 and 14, and the end effector 6 is closed. In this manner, the treatment target is gripped between the gripping pieces 13 and 14. By inputting an operation to make the power supply device 3 supply electric energy to the treatment device 1 with the treatment target being gripped between the gripping pieces 13 and 14, at least one of the high-frequency current and the ultrasonic vibration is applied to the gripped treatment target as treatment energy, as described above.

Further, in this embodiment, the first gripping piece 13 and the vibration transmitting member 8 are formed of a titanium alloy, which has a high vibration transmissibility. Therefore, the vibration generated by an ultrasonic vibrator is effectively transmitted to the treatment surface 17 through the vibration transmitting member 8 and the first gripping piece 13.

Further, in this embodiment, the anti-sticking coating 51 is provided over the treatment surface 17 of the first gripping piece 13. As described above, the anti-sticking coating 51 includes the silane coupling agent, and the silane coupling agent of this embodiment has the molecular chain including a fluorine atom F. Therefore, providing the anti-sticking coating 51 over the treatment surface 17 imparts a function of preventing the sticking of tissue and water repellency to the treatment surface 17.

Further, in this embodiment, the titanate coupling agent used for the organic layer 41 and the silane coupling agent used for the anti-sticking coating 51 are capable of forming a monomolecular film. This allows the organic layer 41 and the anti-sticking coating 51 to be formed to be thin. Forming the organic layer 41 and the anti-sticking coating 51 to be thin can reduce the electrical resistance of the organic layer 41 and the anti-sticking coating 51. Thus, even when the surface of the first gripping piece 13 is subjected to a coating for preventing sticking, a high-frequency current can be effectively applied to the treatment target from the treatment surface 17. That is, according to the treatment device 1 of this embodiment, it is possible to provide the treatment surface 17 with a function of preventing the sticking of a treatment target and to effectively apply a high-frequency current to the treatment target from the treatment surface 17.

Moreover, in this embodiment, the organic layer 41 is provided between the anti-sticking coating 51 and the surface of the first gripping piece 13. The organic layer 41 being bonded to each of the anti-sticking coating 51 and the surface of the first gripping piece 13 allows the anti-sticking coating 51 to adhere to the surface of the first gripping piece 13.

Further, in this embodiment, in the step of applying the titanate coupling agent to the surface of the first gripping piece 13, the modified surface 42 due to the organic functional groups Y of the organic layer 41 is formed over the surface of the first gripping piece 13. In general, silane coupling agents are known to have better bonding properties to organic materials than to titanium. Therefore, by forming the modified surface 42 through the organic layer 41 on the surface of the first gripping piece 13, the adhesion strength of the anti-sticking coating 51 formed by the silane coupling agent to the surface of the first gripping piece 13 is improved as compared with the case where the silane coupling agent is applied directly onto the surface of the first gripping piece 13. The improved adhesion strength of the anti-sticking coating 51 to the surface of the first gripping piece 13 makes the anti-sticking coating 51 less likely to be peeled off, which reduces the rate of deterioration of the anti-sticking coating 51 resulting from friction and heat during treatment. This also improves the durability of the treatment device 1.

In this embodiment, an amine group is used as the organic functional group Y of the titanate coupling agent. Therefore, the durability of the anti-sticking coating 51 is improved as compared with the case where other functional groups are used as the organic functional group Y.

Further, in this embodiment, the organic layer 41 is formed by the titanate coupling agent. Moreover, in this embodiment, the first gripping piece 13 is formed of a titanium alloy. Here, titanate coupling agents are known to have better bonding properties to materials such as titanium than silane coupling agents. Therefore, the organic layer 41 being provided between the anti-sticking coating 51 and the surface of the first gripping piece 13 improves the adhesion strength of the anti-sticking coating 51 formed by the silane coupling agent to the surface of the first gripping piece 13 as compared with the case where the silane coupling agent is applied directly onto the surface of the first gripping piece 13.

The silane coupling agent of this embodiment has the coupling structure at both ends. Therefore, the adhesion strength of the anti-sticking coating 51 to the organic layer 41 and the surface of the first gripping piece 13 is improved as compared with the case where a silane coupling agent having the coupling structure at one end is used.

A method of evaluating the adhesion strength of the anti-sticking coating 51 to the surface of the first gripping piece 13 will now be described. The evaluation of the adhesion strength of the anti-sticking coating 51 to the first gripping piece 13 was carried out, for example, by a sticking test using a simulated tissue simulating a living tissue that is a treatment target. In this sticking test, first, the simulated tissue was incised using the treatment device 1. In the incision of the simulated tissue, an output simulating the output in the incision procedure was performed, and the simulated tissue was incised between the gripping pieces 13 and 14 a predetermined number of times. At this time, for example, output for 2 to 4 seconds was performed a predetermined number of times. Next, using the treatment device 1, the sticking state on the treatment surface 17 was evaluated. In the evaluation of the sticking state, a procedure that may cause sticking of the simulated tissue was performed a predetermined number of times. At this time, for example, output for 2 to 4 seconds was performed a predetermined number of times. After a coagulation treatment, the sticking state of the simulated tissue to the surface of the first gripping piece 13 was evaluated. Then, by repeating the steps of incising the simulated tissue and evaluating the sticking state, the adhesion strength of the anti-sticking coating 51 to the surface of the first gripping piece 13 and the durability of the anti-sticking coating 51 were evaluated.

For example, in the case where no anti-sticking coating is applied to the surface of the first gripping piece 13, that is, where neither the organic layer 41 nor the anti-sticking coating 51 is provided, in the evaluation of the sticking state after approximately 100 times of outputting the treatment energy in incising of the simulated tissue in the above-described sticking test, the simulated tissue stuck to the surface of the first gripping piece 13 was not removed even if the end effector 6 of the treatment device 1 was shaken.

On the other hand, for example, in the case where a silane coupling agent having the coupling structure at one end is applied directly onto the surface of the first gripping piece 13 to provide an anti-sticking coating, in the evaluation of the sticking state after approximately 500 times of outputting the treatment energy in incising of the simulated tissue in the above-described sticking test, the state in which the simulated tissue does not stick to the surface of the first gripping piece 13 or the state in which the simulated tissue stuck to the surface of the first gripping piece 13 can be removed by shaking the end effector 6 of the treatment device 1 was maintained.

In addition, for example, in the case where a silane coupling agent having the coupling structure at both ends is applied directly onto the surface of the first gripping piece 13 to provide an anti-sticking coating, in the evaluation of the sticking state after approximately 700 times of outputting the treatment energy in incising of the simulated tissue in the above-described sticking test, the state in which the simulated tissue does not stick to the surface of the first gripping piece 13 or the state in which the simulated tissue stuck to the surface of the first gripping piece 13 can be removed by shaking the end effector 6 of the treatment device 1 was maintained.

Further, for example, in the case of using the treatment device 1 of this embodiment, in the evaluation of the sticking state, in 1500 times of outputting the treatment energy in incising of the simulated tissue in the above-described sticking test, the state in which the simulated tissue does not stick to the surface of the first gripping piece 13 or the state in which the simulated tissue stuck to the surface of the first gripping piece 13 can be removed by shaking the end effector 6 of the treatment device 1 was maintained.

Figure 6:
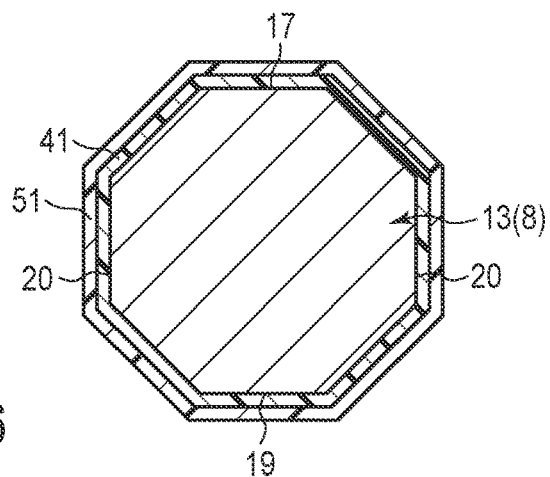
FIG. 6 is a schematic view of a cross section intersecting the longitudinal axis of a first gripping piece according to an exemplary embodiment.

FIG. 6 is a diagram illustrating a first modification of the above embodiment. As shown in FIG. 6, in this modification, the organic layer 41 and the anti-sticking coating 51 are provided in the region where the treatment surface 17 is provided in the extending direction, over the entire periphery around the extended axis (longitudinal axis L) of the gripping piece 13.

In this modification, the organic layer 41 and the anti-sticking coating 51 are also provided on the side surfaces 20 and the back surface 19 in addition to the treatment surface 17 of the gripping piece 13. Therefore, the back surface 19 and the side surfaces 20 as well as the treatment surface 17 are provided with the anti-sticking function and water repellency.

Further, in this modification, the organic layer 41 and the anti-sticking coating 51 are formed over the entire periphery around the extended axis (longitudinal axis L) of the gripping piece 13 in the outer peripheral surface of the gripping piece 13, which facilitates application of the coating agent to the surface of the first gripping piece 13.

Moreover, the organic layer 41 being provided between the anti-sticking coating 51 and the surface of the gripping piece 13 improves the adhesion strength of the anti-sticking coating 51 to the surface of the first gripping piece 13 in this modification as in the first embodiment.

Figure 7:
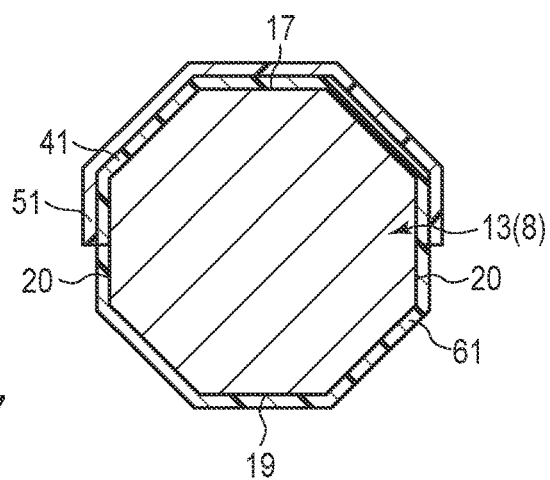
FIG. 7 is a schematic view of a cross section intersecting the longitudinal axis of a first gripping piece according to an exemplary embodiment.

FIG. 7 is a diagram illustrating a second modification of the above embodiment. As shown in FIG. 7, in this modification, a thermal insulation coating (thermal insulation film) 61 is provided on at least a part (for example, the back surface 19 and the side surfaces 20) of the surface of the gripping piece 13 other than the treatment surface 17. The thermal insulation coating 61 is formed from a material having high thermal insulation properties and low thermal conductivity. Further, the thermal insulation coating 61 is preferably made of a material having electrical insulation properties. The thermal insulation coating 61 is formed of, for example a polyetheretherketone (PEEK) resin.

In this modification, the thermal insulation coating 61 being provided on the surface of the gripping piece 13 reduces the thermal harm from the region where the thermal insulation coating 61 is provided on the surface of the gripping piece 13 to living tissue. This prevents the heat generated in the treatment from affecting an unintended living tissue.

Moreover, the organic layer 41 being provided between the anti-sticking coating 51 and the surface of the gripping piece 13 improves the adhesion strength of the anti-sticking coating 51 to the surface of the first gripping piece 13 in this modification as in the first embodiment.

Figure 8:
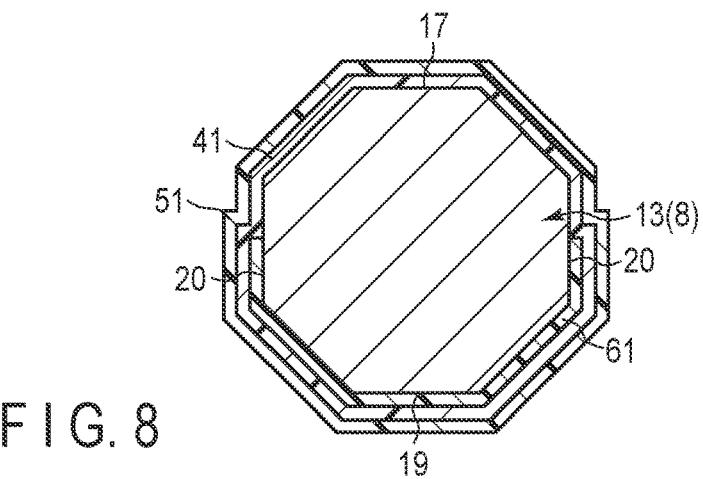
FIG. 8 is a schematic view of a cross section intersecting the longitudinal axis of a first gripping piece according to an exemplary embodiment.

FIG. 8 is a diagram illustrating a third modification of the above embodiment. As shown in FIG. 8, the thermal insulation coating 61 is provided on at least a part of the surface of the gripping piece 13 other than the treatment surface 17 in this modification as in the second modification.

In this modification, the gripping piece 13 is provided with the organic layer 41 and the anti-sticking coating 51 over the entire periphery around the extended axis (longitudinal axis L) of the gripping piece 13 in the outer peripheral surface of the gripping piece 13. At the portion of the surface of the gripping piece 13 where the thermal insulation coating 61 is provided, the organic layer 41 is brought into close contact with the thermal insulation coating 61 from the outside, and the anti-sticking coating 51 is brought into close contact with the organic layer 41 from the outside.

Moreover, the organic layer 41 being provided between the anti-sticking coating 51 and the surface of the gripping piece 13 improves the adhesion strength of the anti-sticking coating 51 to the surface of the first gripping piece 13 in this modification as in the above embodiment.

The coupling structure of the titanate coupling agent of this embodiment also has good bonding properties to an organic material such as a resin. Thus, the organic layer 41 being provided between the anti-sticking coating 51 and the thermal insulation coating 61 improves the adhesion strength of the anti-sticking coating 51 to the surface of the first gripping piece 13 also in the portion where the thermal insulation coating 61 is provided.

Another exemplary embodiment will be described with reference to FIGS. 9 and 10. In this embodiment, the above embodiment is modified as follows. The same parts as in the above embodiment are denoted by the same reference numerals, and the description of these parts is omitted.

Figure 9:
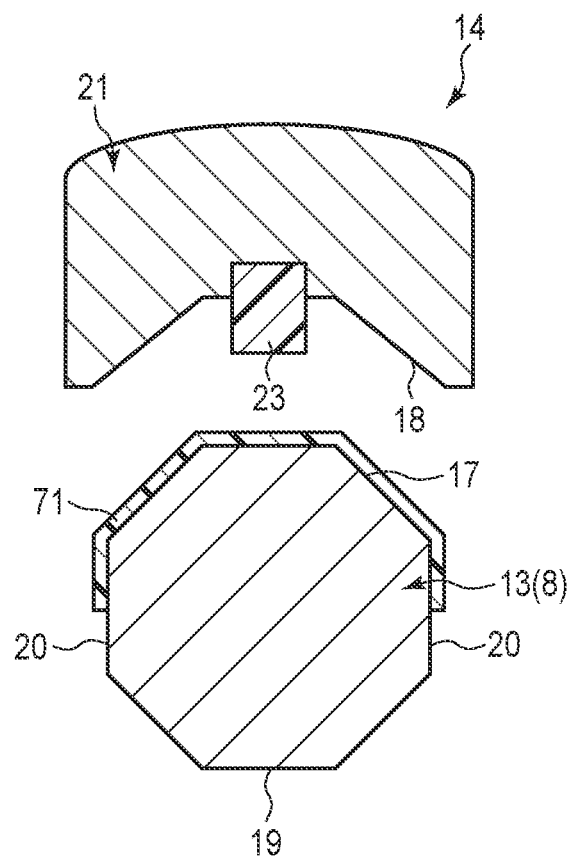
FIG. 9 is a schematic view of a cross section intersecting the longitudinal axis of an end effector according to an exemplary embodiment.
Figure 10:
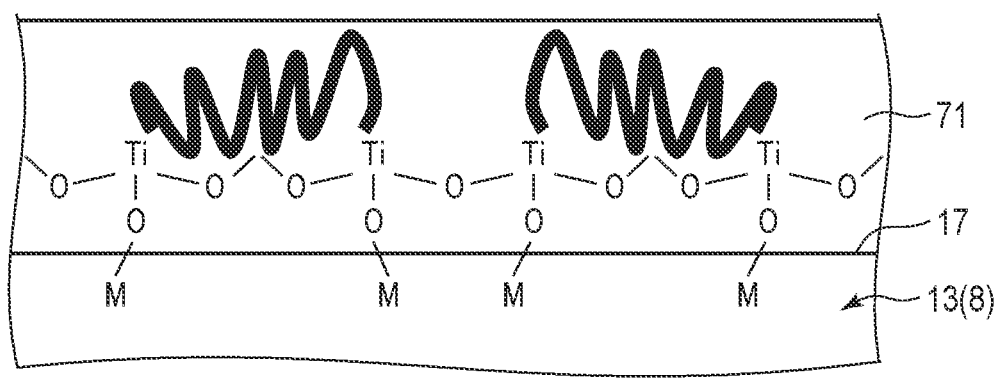
FIG. 10 schematically illustrates a state where an anti-sticking coating is formed over a treatment surface according to an exemplary embodiment.

As shown in FIGS. 9 and 10, in this embodiment, an anti-sticking coating 71 is provided on the surface of the first gripping piece 13. The anti-sticking coating 71 is bonded directly to the surface of the first gripping piece 13.

As shown in FIG. 10, the anti-sticking coating 71 is formed of a material including a titanate coupling agent. The titanate coupling agent of this embodiment includes a titanium atom Ti, a molecular chain containing a carbon atom C and a fluorine atom F, and a hydrolyzable group OR.

In the titanate coupling agent, three hydrolyzable groups OR are each chemically bonded to the titanium atom Ti. In the titanate coupling agent, the three hydrolyzable groups OR being chemically bonded to the titanium atom Ti forms a coupling structure. The coupling structure is provided at each end of the molecular chain.

In the molecular chain, the fluorine atom F or the like is bonded to the carbon atoms C bonded in a chain form. The hydrolyzable group OR is a reactive group which is to be chemically bonded to an inorganic material by hydrolysis etc., and is, for example, an alkoxy group, such as a methoxy group, an ethoxy group, etc.

In the surface of the first gripping piece 13, the coupling structure of the titanate coupling agent is bonded to the surface of the first gripping piece 13. The titanate coupling agent being bonded to the surface of the first gripping piece 13 forms the anti-sticking coating 71 on the surface of the first gripping piece 13.

Here, the bond between the titanate coupling agent and the surface of the first gripping piece 13 includes a chemical bond (by hydrolysis) between the hydrolyzable groups OR of the titanate coupling agent and the hydroxyl groups OH covering the surface of the first gripping piece 13, a bond by chemisorption, a bond by intermolecular force, and a bond by other interactions.

Next, the operation and effect of the treatment device 1 of this embodiment will be described. In this embodiment, the anti-sticking coating 71 is provided on the treatment surface 17 of the first gripping piece 13. As described above, the anti-sticking coating 71 includes the titanate coupling agent, and the titanate coupling agent of this embodiment has the molecular chain including a fluorine atom F. Therefore, in this embodiment as well, providing the anti-sticking coating 71 on the treatment surface 17 imparts an anti-sticking function and water repellency to the treatment surface 17.

Further, in this embodiment, the titanate coupling agent used for the anti-sticking coating 71 is capable of forming a monomolecular film. This allows the anti-sticking coating 71 to be formed to be thin. Therefore, this embodiment, similarly to the above embodiment, makes it possible to provide the treatment surface 17 with a function of preventing the sticking of a treatment target and to effectively apply a high-frequency current to the treatment target from the treatment surface 17.

In addition, in this embodiment, the anti-sticking coating 71 is formed by the titanate coupling agent.

Further, in this embodiment, the first gripping piece 13 is formed of a titanium alloy. Here, titanate coupling agents are known to have better bonding properties to materials such as titanium than silane coupling agents. Therefore, by forming the anti-sticking coating 71 from the titanate coupling agent, the adhesion strength of the anti-sticking coating 71 to the surface of the first gripping piece 13 is improved as compared with the case where the anti-sticking coating 71 is formed from a silane coupling agent.

Further, the titanate coupling agent of this embodiment has a coupling structure at both ends. Therefore, the adhesion strength to the surface of the first gripping piece 13 is improved as compared with the case where a titanate coupling agent having a coupling structure at one end is used.

Figure 11:
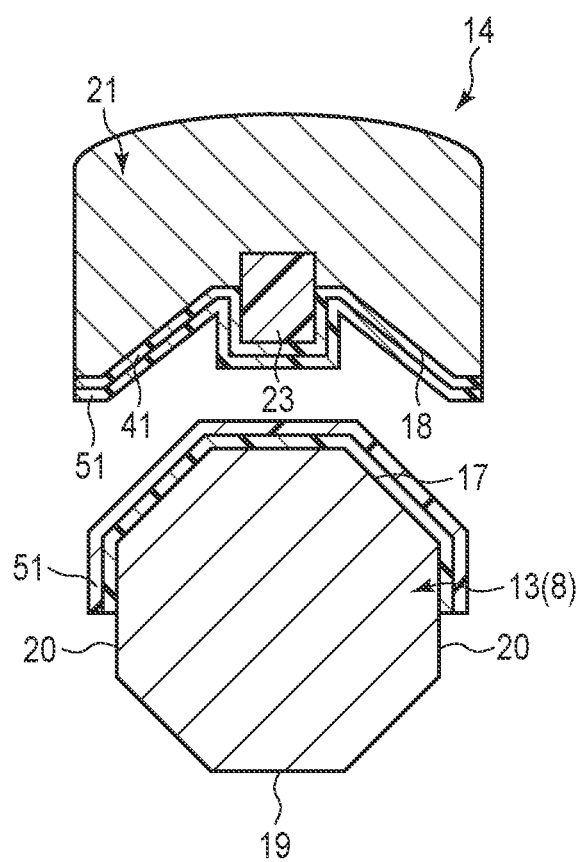
FIG. 11 is a schematic view of a cross section intersecting the longitudinal axis of an end effector according to an exemplary embodiment.

As shown in FIG. 11, in another exemplary embodiment, the organic layer 41 and the anti-sticking coating (second anti-sticking coating) 51 are also provided on the treatment surface 18 of the second gripping piece (gripping member) 14 in the same manner as in the above embodiment. In this case, it is possible to provide the treatment surface 18 of the second gripping piece 14 with a function of preventing the sticking of a treatment target and to effectively apply a high-frequency current to the treatment target from the treatment surface 18.

In other exemplary embodiments, a heat source such as a heater is provided to at least one of the gripping pieces 13 and 14, and heat generated by the heat source is used instead of ultrasonic vibration as treatment energy. In this case, the heat source is attached, from the side opposite to the treatment surface, to a thermally conductive member (e.g., 21) forming at least a part of the treatment surface (e.g., 18). The power supply device 3 is electrically connected to the heat source via an electrical path provided to pass through the inside of the housing 4 and the inside of the shaft 5. The heat source, upon being supplied with electric energy from the power supply device 3, generates heat, and the generated heat is applied to the treatment target through the thermally conductive member (e.g. 21). Also, in this embodiment, both the first gripping piece 13 and the second gripping piece 14 may be attached to the shaft 5 rotatably with respect to the shaft.

In the above-described embodiments and the like, a bipolar energy treatment device (1) having a pair of gripping pieces (13, 14) each of which is provided with an electrode has been described, but the configuration according to the embodiment of the present disclosure is applicable to a monopolar energy treatment device. In this case, the energy treatment device includes an end effector formed of a base material, and the end effector has a treatment surface at least part of which is formed of an electrode. The aforementioned anti-sticking coating is provided over at least the treatment surface of the surface of the base material.

Common Configuration of Embodiments and the Like

An energy treatment device (1) includes: a base (8, 13) including a treatment surface (17) that applies a high-frequency current to a treatment target when being supplied with electric energy, and having electrical conductivity; and an anti-sticking coating (51; 71) which includes a coupling agent having a coupling structure, which is formed on at least the treatment surface (17) of the surface of the base (8, 13) through a bond due to the coupling structure, and which prevents the treatment target from sticking to the surface of the base (8, 13).

A method for manufacturing the energy treatment device (1) includes: forming a base (8, 13) having electrical conductivity and being provided with a treatment surface (17) that applies a high-frequency current to a treatment target when being supplied with electrical energy; forming an organic layer (41) on a surface of the base material (8, 13) by bonding a coupling structure of a titanate coupling agent to the surface of the base (8, 13) on at least the treatment surface (17) of the surface of the base (8, 13); and forming a coating (51; 71) that prevents the treatment target from sticking over the surface of the base (8, 13) by bonding a coupling structure of a silane coupling agent to the organic layer (41).

The present disclosure is not limited to the above-described embodiments, and can be variously modified in practice without departing from the gist the disclosure. Moreover, the embodiments may be suitably combined where possible. In that case, combined effects can be obtained. Further, the above-mentioned embodiments include inventive aspects at various stages, and various inventive aspects can be extracted by an appropriate combination of a plurality of constituent elements disclosed.

The invention claimed is:

1. An energy treatment device comprising:
a base having electrical conductivity and including a treatment surface configured to apply a high-frequency current to a treatment target when supplied with electrical energy;
a coating including a silane coupling agent having a coupling structure, the coating being formed over at least the treatment surface of the base by a bond due to the coupling structure; and
an organic layer that is disposed between the treatment surface of the base and the coating, and is formed as a monomolecular film bonded to the treatment surface of the base,
wherein:
the organic layer includes a titanate coupling agent having a coupling structure,
the coupling structure of the titanate coupling agent is bonded to the treatment surface of the base,
the titanate coupling agent includes a titanium atom, one or more hydrolysable groups chemically bonded to the titanium atom, and an organic functional group chemically bonded to the titanium atom, and
the coupling structure of the silane coupling agent of the coating is bonded to the organic functional group of the titanate coupling agent of the organic layer.

2. The energy treatment device according to claim 1, wherein the silane coupling agent of the coating includes a molecular chain having carbon and fluorine.

3. The energy treatment device according to claim 1, wherein the silane coupling agent of the coating includes the coupling structure at both ends of a molecular chain.

4. The energy treatment device according to claim 1, wherein the base is formed of a titanium alloy.

5. The energy treatment device according to claim 1, wherein the organic layer has a modified surface formed of an amine-based reactive group over the treatment surface of the base.

6. The energy treatment device according to claim 1, further comprising a gripping member that is openable and closable with respect to the base, wherein the high-frequency current flows between the treatment surface and the gripping member when electrical energy is supplied to the base and the gripping member.

7. The energy treatment device according to claim 6, further comprising a second coating including the silane coupling agent having the coupling structure, the second coating being formed on a surface of the gripping member by a bond due to the coupling structure.

8. The energy treatment device according to claim 7, wherein the coating and the second coating are anti-sticking coatings that are configured to prevent sticking of the treatment target.

9. The energy treatment device according to claim 1, further comprising an ultrasonic transducer configured to generate ultrasonic vibration and transmit the ultrasonic vibration to the base when supplied with electrical energy.

10. The energy treatment device according to claim 1, further comprising a thermal insulation coating having thermal insulation properties and provided on a surface of the base other than the treatment surface.

11. The energy treatment device according to claim 10, wherein the thermal insulation coating is formed of a PEEK resin.

12. The energy treatment device according to claim 1, wherein the coating is an anti-sticking coating configured to prevent sticking of the treatment target.

13. An energy treatment device comprising:
a base having electrical conductivity and including a treatment surface configured to apply a high-frequency current to a treatment target when supplied with electrical energy; and
a coating including a titanate coupling agent having a coupling structure, the coating being formed as a monomolecular film over at least the treatment surface of the base and bonded with the treatment surface;
wherein:
the titanate coupling agent includes a titanium atom, a molecular chain containing a carbon atom and a fluorine atom, and at least one hydrolysable group chemically bonded to the titanium atom, and
the coupling structure of the titanate coupling agent of the coating is bonded to the treatment surface of the base.

14. The energy treatment device according to claim 13, wherein the coupling structure is provided at each end of the molecular chain.

15. The energy treatment device according to claim 13, wherein the treatment surface is not covered by a thermal insulation coating.

\* \* \* \* \*